United States Patent [19]
Schulze-Ganzlin et al.

[11] Patent Number: 5,539,799
[45] Date of Patent: Jul. 23, 1996

[54] METHOD AND DEVICE FOR ACCEPTANCE AND STABILITY TESTING OF FILMLESS DENTAL RADIOGRAPHIC EQUIPMENT

[75] Inventors: Ulrich Schulze-Ganzlin, Lorsch; Eriks Blaschka, Weinheim; Josef Plötz, Bensheim, all of Germany

[73] Assignee: Siemens Aktiengesellschaft, Munich, Germany

[21] Appl. No.: 428,161

[22] PCT Filed: Nov. 10, 1993

[86] PCT No.: PCT/DE93/01073

§ 371 Date: Apr. 26, 1995

§ 102(e) Date: Apr. 26, 1995

[87] PCT Pub. No.: WO94/10909

PCT Pub. Date: May 26, 1995

[30] Foreign Application Priority Data

Nov. 12, 1992 [DE] Germany .................. 42 38 268.8

[51] Int. Cl.⁶ .................................. G01D 18/00
[52] U.S. Cl. ............................ 378/207; 378/18
[58] Field of Search ................. 378/207, 18, 176

[56] References Cited

U.S. PATENT DOCUMENTS

| 4,352,020 | 9/1992 | Horiba et al. | 378/18 |
| 5,056,130 | 10/1991 | Engel | 378/207 |

FOREIGN PATENT DOCUMENTS

| 0460749 | 6/1991 | European Pat. Off. . |
| 0506559 | 3/1992 | European Pat. Off. . |
| 3642565 | 6/1987 | Germany . |

*Primary Examiner*—Don Wong
*Attorney, Agent, or Firm*—Hill, Steadman & Simpson

[57] ABSTRACT

In a method for acceptance and stability testing of filmless dental radiographic equipment a test measurement body having a plurality of absorption elements which absorb differently is arranged in the beam path of the X-rays at a defined close distance from a radiation-sensitive sensor. The electric signals obtained from the sensor are fed to a computing unit which processes these to form image value signals which are then fed either directly to a display unit or are firstly compared with prescribed desired image values and, in the case of deviations, fed to the display unit. The test measurement body includes a holder for reproducibly holding a sensor which can be applied intraorally to a patient.

10 Claims, 5 Drawing Sheets

METHOD AND DEVICE FOR ACCEPTANCE AND STABILITY TESTING OF FILMLESS DENTAL RADIOGRAPHIC EQUIPMENT

BACKGROUND OF THE INVENTION

1. Field of the Invention

The present invention as directed to a method and a device for acceptance and stability testing of filmless dental radiographic equipment.

2. Description of the Prior Art

German OS 36 42 565 discloses for the purpose of stability testing of dental radiographic equipment which is operated in conjunction with an X-ray film a device which comprises a test body having a radiation-absorbing staircase made from a plurality of elements of different absorbing capacity. A depression into which an X-ray film can be inserted is located in the test body. The test device can be mounted on the tube of radiographic equipment and holds a centring aid suitable for this purpose.

Furthermore, U.S. Pat. No. 4,352,020 discloses a computed tomography apparatus in which for the purpose of stability testing of the characteristic properties of detectors it is possible for a multiplicity of so-called phantom elements of different absorptive capacity to be brought into the beam path of the X-ray source. In order to establish deviations of the detectors, radiation is applied to the latter, once without and after with phantom elements inserted into the beam path. The comparative values thus obtained are evaluated in a computing unit and displayed on a display.

In the case of filmless dental radiographic equipment, in which the X-ray radiograph is recorded by a sensor, for example a CCD sensor, the need exists, as in the case of the present day X-ray film technology to submit the sensor to checking, specifically once during acceptance of the equipment and later at regular intervals. In the case of the (stability) test to be provided at regular intervals, which is usually carried out by the operator of the radiographic equipment, it can be concluded whether the radiograph-producing system has remained stable within fixed limiting deviations.

An object of the present invention is to specify a test method tuned to such filmless dental radiographic equipment.

The above object is achieved in accordance with the principles of the present invention in a method and an apparatus for acceptance and stability testing of filmless dental radiographic equipment wherein a test measurement body having a number of absorption elements with respectively different radiation absorption characteristics is disposed in the beam path of incoming x-rays at a defined close proximity from a radiation sensor, and wherein electrical signals obtained from the sensor due to the radiation incident thereon are supplied to a computing unit which processes these signals to form image value signals, and wherein the image value signals are fed either directly to an output unit, such as a monitor or a printer, or are first compared with prescribed desired image values and, in the case of deviations from the prescribed values, the deviating values are supplied to the output unit.

An advantage of the invention is that the inventive method and apparatus permit computer-aided analysis of the measurement results. A subjective, visual assessment can be further supported or supplemented thereby.

The method proposed according to the invention can be applied both to dental radiographic equipment having sensors which can be placed intraorally and to dental radiographic equipment by means of which panoramic tomographs or remote X-ray images can be made. Accordingly, the test measurement body can be advantageously configured in such a way that it is suitable both for reproducibly holding a sensor which can be applied intraorally and for holding on the secondary diaphragm of a panoramic tomographic camera.

In application with equipment having a sensor which can be applied intraorally, it is advantageous to fit the test measurement body with a sensor holder which permits the sensor to be held at a close defined distance, for example of a few millimeters, from the edge of the tube and to be rotated advantageously about the axis of the tube in specific angular degree steps. The sensor holder fixes the sensor at the prescribed distance relative to the center of rotation.

PREFERRED EMBODIMENTS

Figure 1:
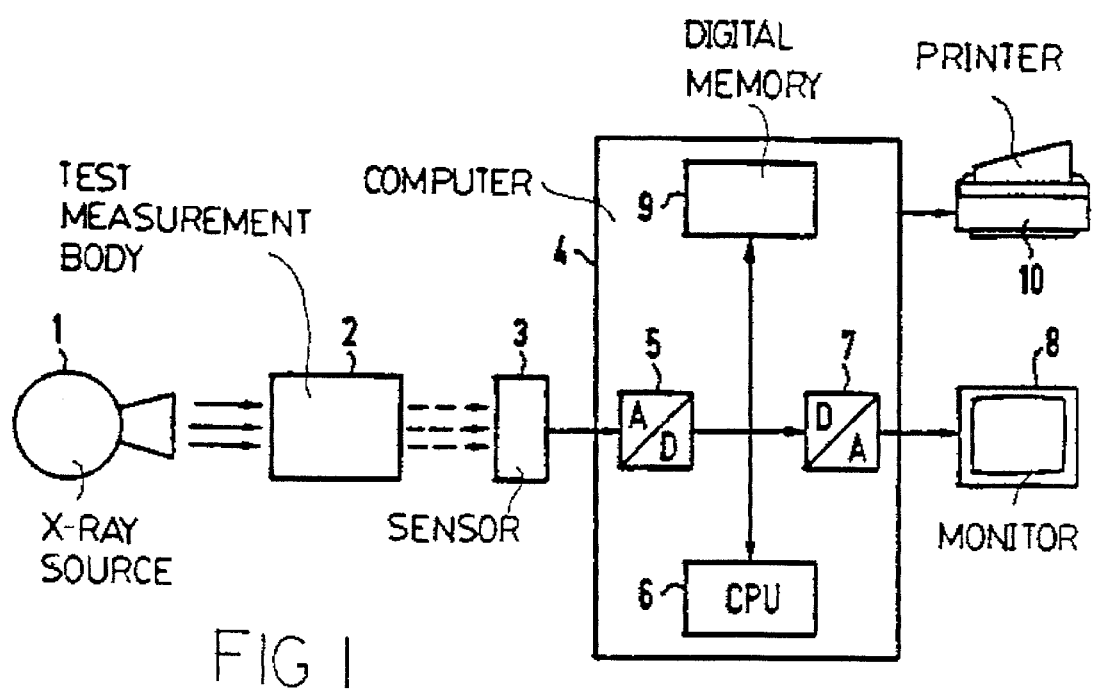
FIG. 1 shows a block diagram for explaining a method.

The method according to the invention is firstly described in more detail with the aid of FIG. 1. The X-radiation emanating from an X-ray source denoted generally by 1 penetrates a test measurement body 2, which is explained in still further detail with the aid of the following figures, and then impinges on a sensor 3 which converts the X-radiation into electric signals. The latter are fed to a computer 4 and converted by means of an A/D converter 5 into digital signals which are then processed in a processor 6 to form image signals or image values. These are subsequently fed either directly via a D/A converter 7 to a display unit 8 in the form of a monitor, or firstly compared with desired image values stored in a digital memory 9 and, in the case of deviations, fed to the display unit 8. A display unit 10 in the form of a printer can be provided as an alternative or an addition to the monitor.

Figure 2:
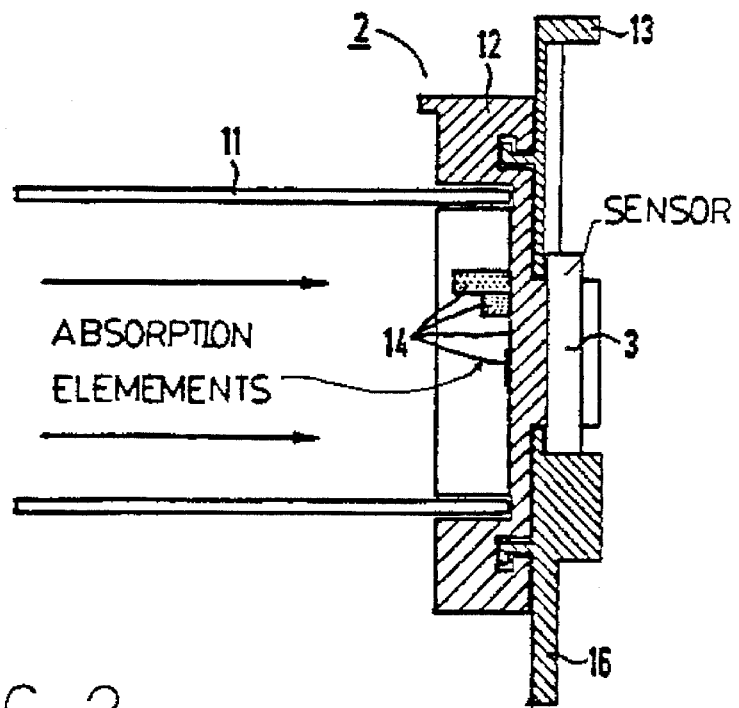
FIG. 2 shows the device according to the invention being applied in the case of radiographic equipment having a sensor which can be applied intraorally, in section along the line II/II in FIG. 3.

FIG. 2 shows in a sectional representation an embodiment of the test measurement body 2 for acceptance and stability testing of a sensor which can be applied to a patient intraorally and to which an extraorally arranged X-ray source is applied. In the case of such dental radiographic equipment, the X-ray source has in general a cylindrical tube end. The test measurement body 2 is plugged onto the tube end, denoted in FIG. 2 by 11.

The test measurement body 2 comprises two housing parts 12 and 13, a fixed housing part 12 which can be plugged onto the tube end 11 and accommodates a plurality of absorption elements 14, and a housing part 13 which can be rotated with respect to the fixed housing part 12 and on which the sensor 3, which can be applied per se to a patient intraorally, is held in a reproducible fashion. The absorption elements 14, which are explained in still further detail in one of the following figures, should be arranged as close as possible in front of the sensor, in order to avoid possible parallax errors.

Figure 3:
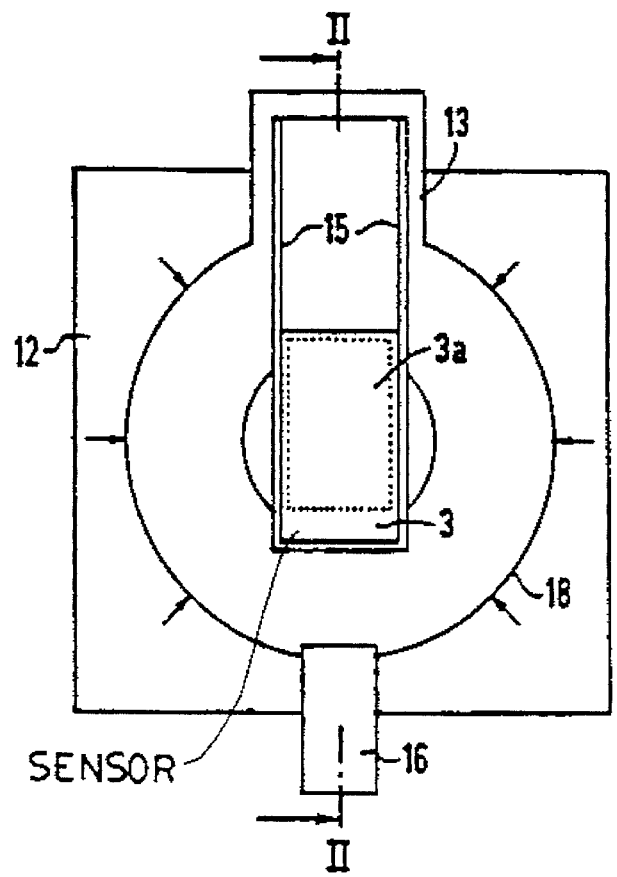
FIG. 3 shows a device according to FIG. 2, in elevation.

In conjunction with the representation according to FIG. 3, which shows the test body 2 in front view, it follows that the sensor 3 or its active surface 3a, indicated by dots, is arranged centrally at the tube outlet. In the position represented, the central beam thus runs perpendicularly through the center of the active sensor surface and parallel to the surface normal. The angular alignment is fixed by a guide denoted by 15.

Figure 4:
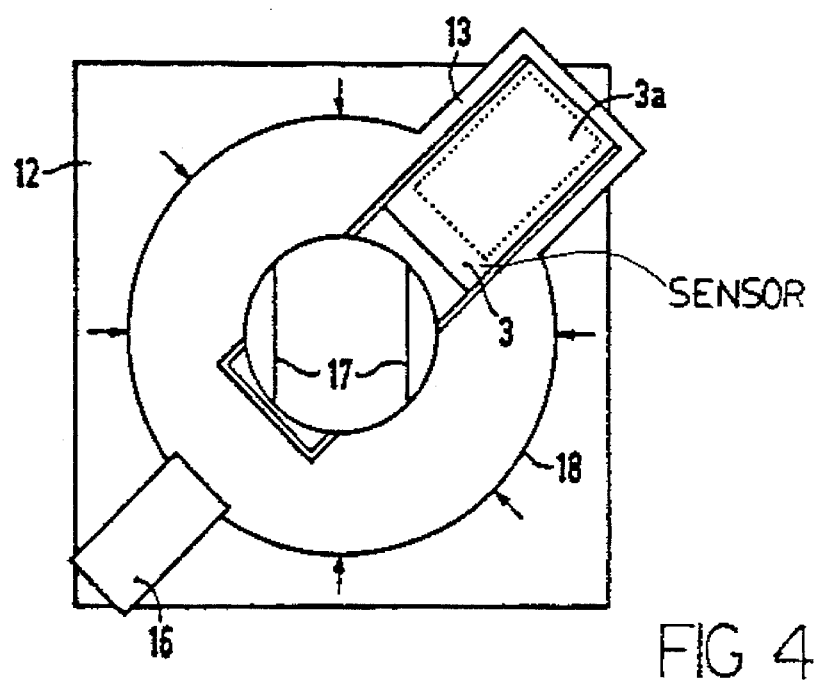
FIG. 4 shows the device according to FIG. 3 in a position rotated by 45°.

As indicated by arrows which are not denoted in more detail, the housing part 13 in which the sensor 3 is fixed can be rotated in 45° steps and fixed in a latching fashion in the respective positions. A handle 16 is provided for adjustment on the underside of the housing part 13. Rotation of the housing part 13 is, however possible only when the sensor 3 is brought along the guide 15, that is to say in the radial direction, out of the basic position shown in FIG. 3 into the position shown in FIG. 4. In this position, the sensor 3 comes to be situated outside lateral guide parts which are denoted by 17 in FIG. 4 and attached to the fixed housing part 12. The edge of the radiation field can be measured in this second position, in which the active surface 3a of the sensor 3 covers the edge of the radiation field indicated by 18. The sensor is also held here in a reproducible fashion in the guide 15. The active sensor surface 3a covers the useful ray only partly, as a result of which the extent of the edge of the field can be analyzed and measured via the computer (for example via a PC).

In order to measure the entire edge, it is necessary to guide the sensor over the edge in a plurality of steps (in 45° steps in the exemplary embodiment here). Test software contained in the computing unit 4 can include all the relevant coordinates for a measurement analysis. The distance between the center of rotation and the active sensor edge can be interrogated by the test software so that the geometrical relationships are known to the system for calculating purposes. It is now possible with each angle setting to carry out a recording which is acquired by the digital system, represented and evaluated. In this case, the distance between the center of rotation and the edge of the radiation field is automatically measured and compared with desired values. For the case already outlined at the beginning of direct display on the monitor 8, it can be advantageous for the purpose of supporting the visual check additionally to insert into the test recording on the monitor a desired zone of the edge of the field in the form of a circular segment.

The angular steps can also be selected to be narrower in order to obtain a finer evaluation of the edge of the radiation field.

Figure 8:
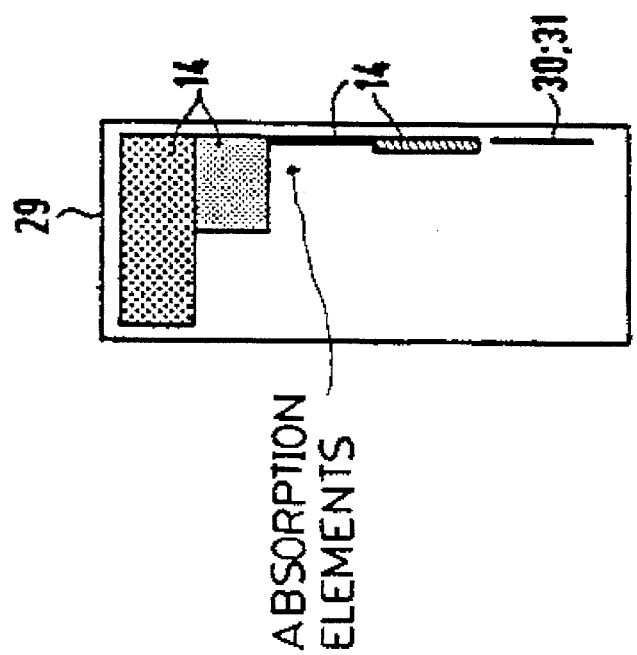
FIGS. 7 and 8 show a test measurement body used in the device according to FIGS. 2 to 4 in plan view and side elevation.
Figure 7:
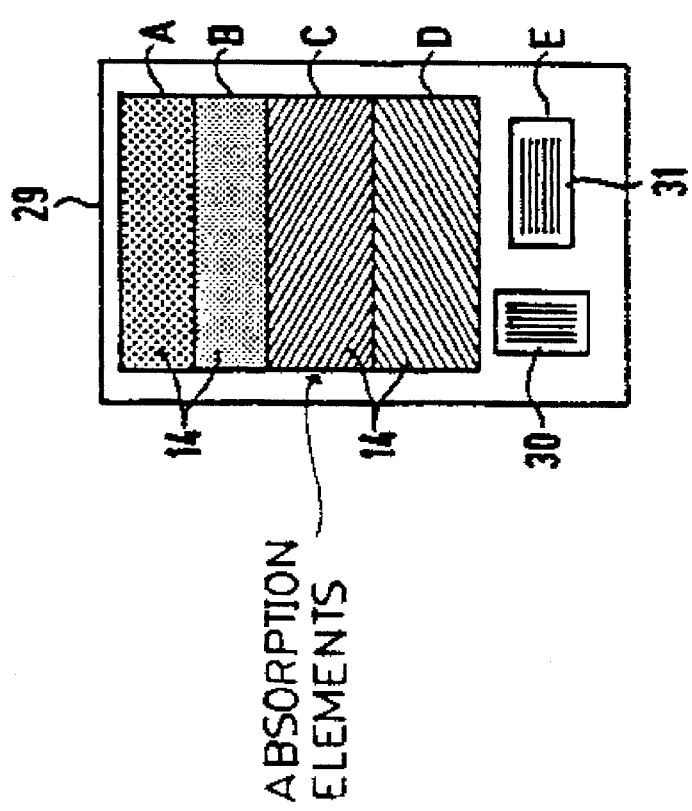

The arrangement of the absorption elements 14 which contains the test measurement body 2 may be seen from FIGS. 7 and 8. It will be described in further detail later.

Figure 6:
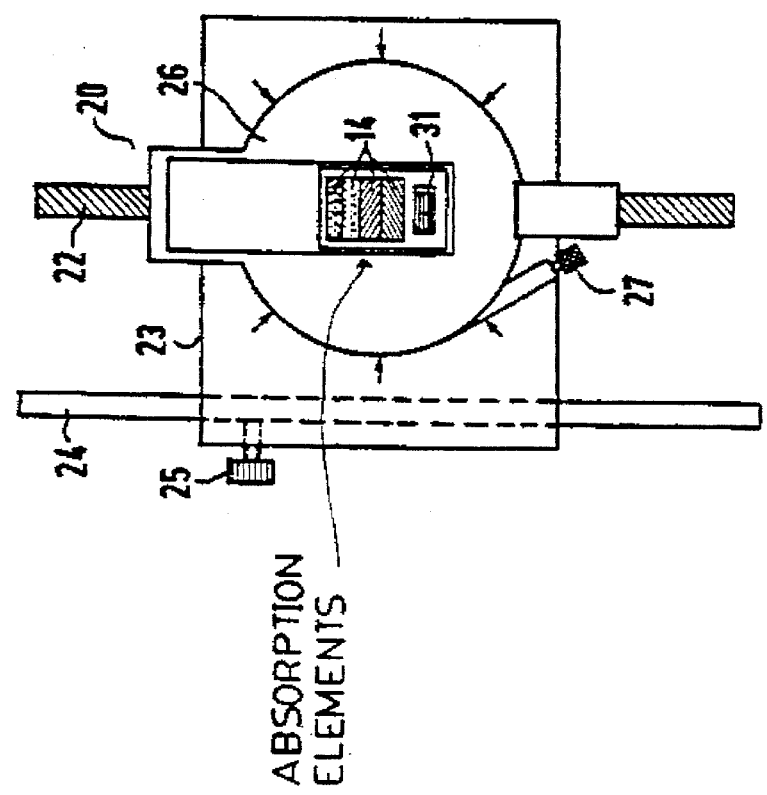
FIGS. 5 and 6 show the device according to the invention being applied in the case of panoramic radiographic equipment.
Figure 5:
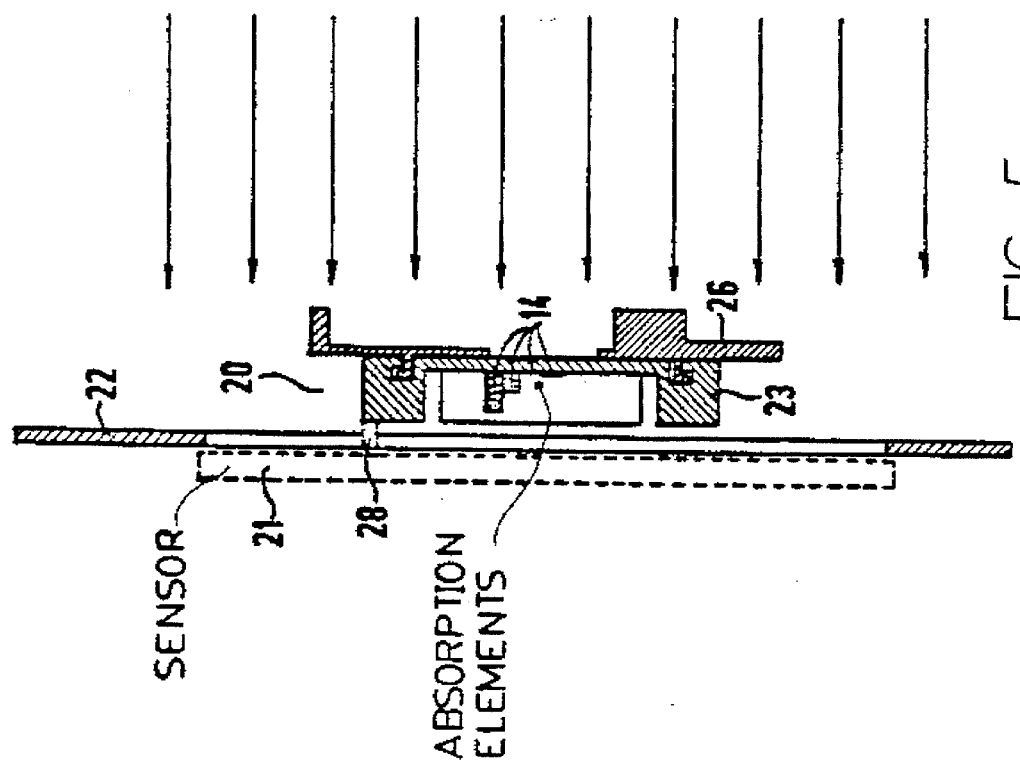

FIGS. 5 and 6 show an embodiment which is suitable for enabling acceptance and stability testing in the case of filmless dental radiographic equipment for making panoramic tomographs using the slot technique. The test measurement body 20 which comes to be used here is of similar construction to the test measurement body 2 described previously; however, it differs with regard to how it is held on the radiographic equipment and with regard to the arrangement of the lead line patterns.

The sensor 21 to be tested is preferably a CCD which is arranged closely adjacent to the secondary diaphragm 22 and covers the slot thereof. In the case of such a CCD, the signals are formed by integration of the charges generated, it being the case that the charges are moved on in the cycle transverse to the slot of the secondary diaphragm according to the cycle of motions of the panoramic tomographic camera.

Although, as is represented in FIGS. 7 and 8, the test measurement body 20 can contain below the stepped absorption elements 14 two lead line patterns (positions 30 and 31), which are arranged offset by 90° relative to one another (FIG. 7), it can be advantageous in acceptance and stability testing of panoramic radiographic equipment to provide only a single lead line pattern having gratings extending transverse to the slotted diaphragm. The starting point in this case is the following consideration:

In panoramic tomographic cameras, it is advantageous to use for the purpose of measuring the modulation transfer lead line patterns whose gratings are arranged perpendicular to one another. The lead line patterns are arranged simultaneously and without overlap in the beam path just in front of the active surface of the detector, or are brought there one after another.

In order to determine the modulation transfer transverse to the secondary diaphragm slot, the X-ray intensity is temporarily modulated using suitable means, for example by electronic control of the generator or by a rotating sector diaphragm having sectors which are alternately free and occupied by lead. In this case, the period corresponds to the time for the movement of a pixel in the cycle of motions of the panoramic tomographic camera transverse to the secondary diaphragm slot by a periodic length of the grating arranged along the secondary diaphragm slot. Modulated sensor signals having a modulation depth corresponding to the modulation transfer are obtained in this way.

In order to determine the modulation transfer along the secondary diaphragm slot, X-radiation is simply applied to the sensor through the grating arranged transverse to the secondary diaphragm slot. The problem, arising in practical application, that the grating must in this case be adjusted very accurately with respect to the direction of movement of the panoramic tomographic camera is solved by the following modifications: measurement is performed with the cycle of motions stopped and with the sensor control cycle likewise stopped, or the sensor is irradiated by a single X-ray pulse whose pulse duration is relatively short compared to the time in which a pixel moves transversely over the secondary diaphragm slot.

In the case of the use of a lead line pattern whose line distance is not large as against the extent of individual detector elements determining the resolution, the modulation transfer depends on the (spatial) phase relation between the pattern lines and detector elements. Here, it is advantageous to rotate the lead line pattern by a small angular amount, for example 5°, out of the direction to be measured, so that the most varied phase relations occur over the extent of the sensor, as a result of which it is possible, for example, to determine the maximum modulation transfer by computer-aided analysis.

In the embodiment shown in FIG. 6, the test measurement body 20 can be adjusted along the slot of the secondary diaphragm 22. For this purpose, the non-rotatable housing part 23 of the test measurement body 20 can be moved along a guide rod 24 mounted on the radiographic equipment, and can be fixed in various positions by a mounting screw 25.

The absorption elements 14 and the lead line pattern 31 can thus be brought into various positions relative to the sensor 21. With the aid of a latching device which is not shown in the drawings, for example a ball-type latching device, the rotatable housing part 26 can be rotated in 45° steps, and thus also by 90°, in the latching fashion. Measurements parallel and perpendicular to the TDI direction are thus possible. In order to bring the lead line pattern 31 into position for a measurement in the way explained above for determining the modulation transfer, a fine adjustment is provided in addition, which permits the lead line pattern to be adjusted by approximately 5° in order in this way to be able to set various phase relations between the grating of the lead line pattern and the sensor matrix. This fine adjustment can be undertaken, for example, with the aid of a setting screw 27 which acts on the abovementioned ball-type latching device and displaces the latter by the abovementioned 5 angular degrees. Alternatively, it is also possible to provide a fine adjustment in the form of a threaded toothing or the like.

As discussed above, it is also conceivable as an alternative to provide two lead line patterns and to arrange the test measurement body 20 to be fixed, that is to say not adjustable along the slot of the secondary diaphragm. This can be accomplished in a suitable way, for example by providing the non-rotatable housing part 23 with a mounting hook 28 (illustrated by dashes in FIG. 5), which reaches through the slot of the secondary diaphragm and fixes the test body to the sensor at a defined close distance.

The absorption elements 14 are to be arranged in such a way that they do not overlap in the course of a test recording. The elements must be arranged perpendicular to the direction of integration for the purpose.

FIGS. 7 and 8 show the arrangement of the absorption elements of the test measurement body in plan view and side elevation for the case of application to equipment with a sensor which can be applied intraorally. The absorption elements 14 form a measuring field arrangement 29 in which, seen from above, at first three fields A, B and C are provided with attenuating elements which are graded with respect to their absorptive response in accordance with the X-ray film method in such a way that they would cause a density grading in a ratio of 1:1.25:1.5 af (=above fog) during a film exposure. This grading serves the purpose of determining a function between the dose and the digitized measuring signal. The signal noise or deviations from a standard can also be established with the aid of deviations from images in the region of grade A. Deviations from the standard can be established with respect to the contrast with the aid of the two fields A and D. The modulation transfer can be determined in the case of a specific spatial absorption modulation with the aid of the field E, which contains the abovementioned two lead line patterns 30, 31 whose gratings are arranged perpendicular to one another.

Figure 11:
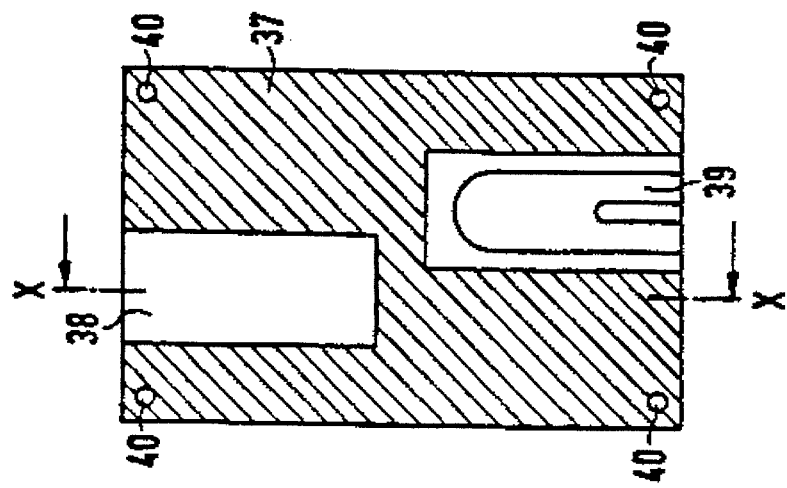
FIGS. 9 to 11 show a further advantageous variant of a test measurement body in various views.
Figure 10:
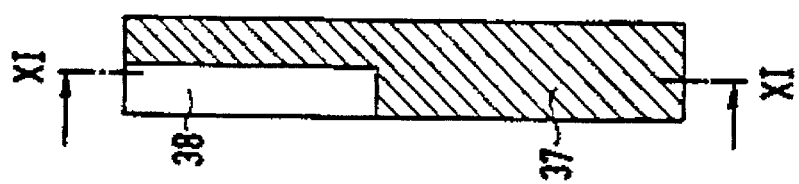
Figure 9:
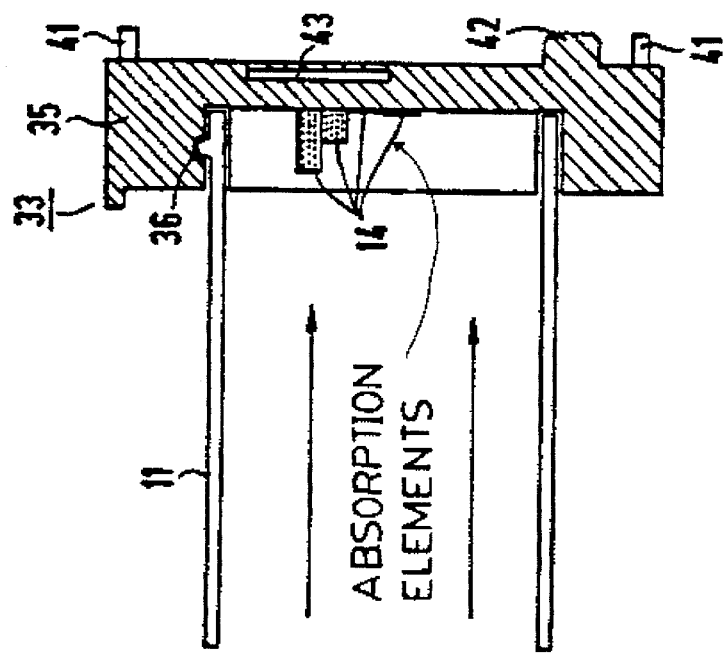

FIGS. 9 to 11 show a further advantageous embodiment of a test measurement body. The test measurement body 33 of this variant includes a housing part 35, which in contrast to the previously explained variants is not fixed but can be rotated with respect to the tube 11 in a plurality of steps, preferably in 45° steps, and is arranged in a latchable fashion in the individual positions. A suitable latching device denoted by 36 in FIG. 9, for example in the form of a ball-type latching device, can be provided for this purpose. A second housing part 37, which is represented in FIG. 10 from the side and in FIG. 11 from the front in section and is a support for the sensor used can be mounted on the housing part 35. In order also to be able to use the test body for sensors which are differently contoured, the housing part 37 includes a plurality of differently shaped cutouts 38, 39 into which the sensors can be alternatively inserted. The cutouts 38, 39 are arranged in such a way that the active surface of the inserted sensors is correspondingly situated opposite the absorption elements, on the one hand, and covers the edge of the radiation field, on the other hand. The edge of the radiation field can be detected in its entirety by means of a plurality of measurements accompanied by rotation of the housing part 35 in the abovementioned way, and thus a possibly impermissible deviation from a fixed standard can be established.

For the purpose of fixing or holding on the housing part 35, the housing part 37 includes four bores 40 in which correspondingly shaped pins 41 on the housing 35 engage. The housing part 37 can thus be mounted on the part 35 in two positions rotated by 180°, a projection 42 provided on the part 35 preventing the user from inadvertently introducing the sensor provided for the test into the wrong cutout (here, the cutout 39). If the housing part 37 is plugged on rotated by 180°, the projection 42 reaches into the cutout 38 and thus prevents the sensor from being introduced into this cutout. A further distinguishing feature of this embodiment is that the housing part 35 is further provided with a transverse slot 43 which is constructed and arranged in such a way that an X-ray film normally used, typical formats being 2×3 cm to 3×4 cm, can be introduced and positioned with respect to the absorption elements. It is therefore possible to carry out a stability test not only for filmless dental radiographic equipment but also for equipment with X-ray film such as is presently in use.

Although modifications and changes may be suggested by those skilled in the art, it is the intention of the inventors to embody within the patent warranted hereon all changes and modifications as reasonably and properly come within the scope of their contribution to the art.

We claim:

1. In a filmless dental radiographic installation having an x-ray tube and an intraoral sensor which generates electrical signals corresponding to x-rays incident thereon, the improvement comprising:

a test measurement body having a plurality of absorption elements which have respectively different x-ray absorption characteristics;

a holder for holding said test measurement body between said x-ray tube and said sensor at a predetermined close distance from said intraoral sensor, said holder comprising means for attaching one side of said holder to said tube of said x-ray source and for attaching an opposite side of said holder to said sensor;

a display unit; and computer means, supplied with said electrical signals from said intraoral sensor, for forming image value signals from said electrical signals and for optionally feeding said image value signals directly to said display unit or for first comparing said image value signals with predetermined image values and, if said image value signals deviate from said predetermined image values, feeding said image value signals to said display unit.

2. The improvement of claim 1 wherein said holder comprises:

a first housing part attachable to said x-ray tube and containing said test measurement body;

a second housing part having a plurality of recesses therein for respectively receiving sensors of different shapes with only one sensor being used at a time;

means for relatively orienting said second housing part relative to said first housing part to position one of said recesses, containing said sensor, at said predetermined close distance from said test measurement body; and locking means carried on said first housing part and interacting with a recess in said second housing part not containing a sensor for preventing a sensor from being inserted into that recess.

3. The improvement of claim 2 wherein said means for relatively orienting said second housing part relative to said first housing part comprises means for permitting rotation of said second housing part relative to said x-ray tube.

4. The improvement of claim 3 wherein said second housing part can assume a plurality of different rotary positions relative to said x-ray tube, and further comprising means for reproducible identifying said rotary positions.

5. The improvement of claim 2 wherein said second housing part comprises a slot for receiving standard intraoral x-ray film.

6. In a filmless dental radiographic installation having an x-ray tube and an extraoral sensor which generates electrical signals corresponding to x-rays incident thereon, and including a secondary diaphragm disposed between said x-ray tube and said extraoral sensor, the improvement comprising:

a test measurement body having a plurality of absorption elements which have respectively different x-ray absorption characteristics;

a holder for holding said test measurement body between said x-ray tube and said sensor at a predetermined close distance from said extraoral sensor, said holder comprising means for attaching said test measurement body to said secondary diaphragm at said predetermined close distance from said extraoral sensor;

a display unit; and computer means, supplied with said electrical signals from said extraoral sensor, for forming image value signals from said electrical signals and for optionally feeding said image value signal directly to said display unit or for first comparing said image value signals with predetermined image values and, if said image value signals deviate from said predetermined image values, feeding said image value signals to said display unit.

7. The improvement of claim 6 wherein said sensor extraoral has a measuring field having a center, and wherein said holder comprises means for selectively orienting said test measurement body in a first position, disposed centrally relative to said measuring field, and in a second position disposed decentrally relative to said measuring field at which said sensor extraoral detects an edge of said x-ray beam.

8. The improvement of claim 7 wherein said means for orienting comprise a radially extending guide for said test measurement body.

9. The improvement of claim 8 wherein said holder comprises a first housing part mountable on an end of said x-ray tube and containing said test measurement body, and a second housing part, mounted so as to rotatable relative to said first housing part, which contains said extraoral sensor.

10. The improvement of claim 9 wherein said second housing part is rotatable through 360° relative to said first housing part, and said holder comprising means for latching said second housing part into a plurality of selected angular positions relative to said first housing part.

* * * * *